United States Patent [19]

Mori

[11] 4,304,688

[45] Dec. 8, 1981

[54] LIQUID AROMATIC DEODORIZING COMPOSITION

[75] Inventor: Yasuyuki Mori, Tanabe, Japan

[73] Assignee: Duskin Franchise Co. Ltd., Osaka, Japan

[21] Appl. No.: 218,638

[22] Filed: Dec. 22, 1980

[30] Foreign Application Priority Data

Dec. 18, 1979 [JP] Japan ................................ 54-163533

[51] Int. Cl.³ ............................................... A61K 7/46
[52] U.S. Cl. ............................................... 252/522 R
[58] Field of Search ................................... 252/522 R

[56] References Cited

U.S. PATENT DOCUMENTS 2,902,510 9/1959 Webb ............................... 252/522 R
3,510,536 5/1970 Brennan .......................... 252/522 R Primary Examiner—John F. Niebling
Attorney, Agent, or Firm—Sherman & Shalloway

[57] ABSTRACT

Disclosed is a liquid aromatic deodorizing composition comprising a solution containing an isoparaffin type hydrocarbon having an initial boiling point higher than 150° C. and a final boiling point lower than 300° C. and a perfume at a weight ratio of from 95/5 to 50/50. This deodorizing composition has a uniform perfume-releasing property and is excellent in the durability of the aromatic deodorizing effect.

2 Claims, 2 Drawing Figures

LIQUID AROMATIC DEODORIZING COMPOSITION

BACKGROUND OF THE INVENTION (1) Field of the Invention

The present invention relates to a liquid aromatic deodorizing composition. More particularly, the present invention relates to a novel liquid aromatic deodorizing composition which has a uniform aroma-releasing property and a gradual aroma-releasing property and which is excellent in the durability of the aromatic deodorizing activity.

(2) Description of the Prior Art

Most of commercially available liquid aromatic deodorizing agents comprise a perfume incorporated and dispersed in a solvent such as ethanol/water with a nonionic surface active agent and are used in the state where they are packed in vessels having an evaporation plate as shown in FIG. 1.

As another type of the conventional aromatic deodorizing agent, there can be mentioned a deodorizing agent comprising a perfume adsorbed in an aqueous gel of gelatin or carragheenin or an adsorbent such as silica gel or alumina gel. The deodorizing agent of this type is defective in that the effective period during which a perfume is released in a room or the like is short and since the perfume is held in an adsorbent or the like, the perfume is readily chemically deteriorated and the aroma is degraded while the deodorizing agent is used. On the other hand, a liquid aromatic deodorizing agent is free of such defect of deterioration of the perfume and the period during which the perfume is released is relatively long. Therefore, such liquid aromatic deodorizing agents have habitually been used.

Such liquid aromatic deodorizing agents, however, are defective in that in the initial stage, the consumption rate of the liquid aromatic deodorizing agent is very high and in the subsequent stage, the activator which is a nonvolatile substance is accumulated on the evaporation plate of the vessel to drastically reduce the property of releasing the liquid aromatic deodorizing agent, with the result that the property of releasing the aroma at a constant rate durably for a long time cannot be obtained. Furthermore, since the perfume is forcibly dispersed in a water-containing solvent with use of a surface active agent, the deodorizing composition is readily frozen in winter or a trouble such as phase separation takes place.

SUMMARY OF THE INVENTION

I found that when an isoparaffin type solvent having an initial boiling point higher than 150° C. and a final boiling point lower than 300° C. is used as the solvent for a liquid aromatic deodorizing composition, the above-mentioned defects are eliminated and the durability of the aromatic deodorizing activity of the liquid aromatic deodorizing composition is highly improved.

It is therefore a primary object of the present invention to provide a liquid aromatic deodorizing composition having a certain perfume-releasing rate and a gradual perfume-releasing property and hence, being excellent in the durability of the aromatic deodorizing activity.

Another object of the present invention is to provide a liquid aromatic deodorizing composition in which occurrence of troubles such as phase separation and freezing in winter is prevented and an excellent safety is retained.

In accordance with the present invention, there is provided a liquid aromatic deodorizing composition having a uniform releasing property, which comprises a solution containing an isoparaffin type aromatic hydrocarbon having an initial boiling point higher than 150° C. and a final boiling point lower than 300° C. and a perfume at a weight ratio of from 95/5 to 50/50.

DETAILED DESCRIPTION OF THE PREFERRED EMBODIMENTS

The most important feature of the present invention is that an isoparaffin type hydrocarbon having the above-mentioned specific fractionating property is used as the solvent. More specifically, if an isoparaffin type hydrocarbon having an initial boiling point higher than 150° C. and a final boiling point lower than 300° C. is used as the solvent, a perfume can be dispersed without using a surface active agent or other non-volatile component.

All of isoparaffin type hydrocarbons having an initial boiling point higher than 150° C., preferably higher than 160° C., and a final boiling point lower than 300° C., preferably lower than 270° C., may be used as the solvent in the present invention. When such specific isoparaffin type hydrocarbon is selected and used as the solvent, the perfume is released at an appropriate evaporation rate, and furthermore, since release of the perfume is performed without any change of the composition of the solution, an excellent durability of the aromatic deodorizing activity is attained. Moreover, since a non-volatile component such as a surface active agent is not contained, even if the deodorizing composition is used over a long period, reduction of the perfume-releasing property owing to clogging of the evaporation plate of a vessel with a non-volatile component is not caused at all, and a constant and durable aromatic deodorizing effect can be obtained. Still further, since the perfume is not forcibly dispersed in the solvent with a surface active agent or the like but the perfume per se is readily dissolved in the solvent, incorporation of a substance having a high pour point is obviated. Since the above-mentioned isoparaffin type hydrocarbon ordinarily has a pour point lower than −60° C., freezing is not caused even if the deodorizing composition is used during a long period in the cold district. Furthermore, since the flash point of the above-mentioned isoparaffin hydrocarbon is ordinarily higher than 50° C. and particularly higher than 80° C., there is no risk of a fire and the safety of this solvent to the human body is higher than that of other solvents.

Any of perfumes soluble in the above-mentioned isoparaffin type solvent can be used in the present invention. For example, there can be used natural and synthetic perfumes such as refined oils, e.g., camphor oil, cassia oil, bois de rose oil, clove oil, eucalyptus oil, cedar oil, sandalwood oil, star aniseed oil, ylang-ylang oil, lemon oil, orange oil, bergamot oil, lavender oil, patchouli oil, citronella oil, lemongrass oil, vetiver oil, rose oil and geranium oil, animal perfumes, e.g., musk, castreum and amber gris, synthetic perfumes, e.g., vaniline, methyl salicylate, cinnamylaldehyde, β- phenylethyl alcohol, hydroxycitronellal, phenylacetaldehyde and piperonal, and mixtures of two or more of the foregoing perfumes.

Figure 1:
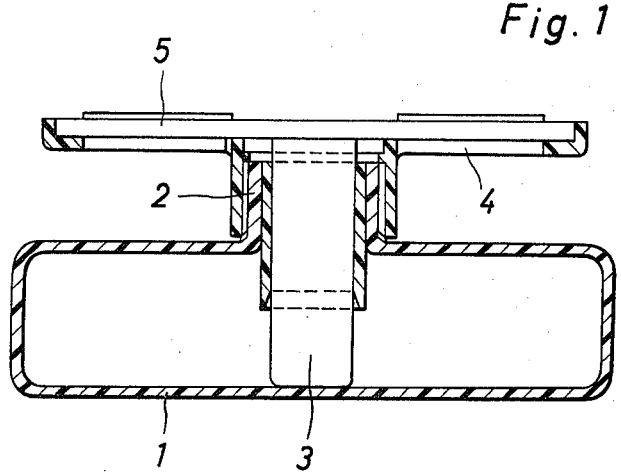
FIG. 1 is a sectional view illustrating a vessel in which a liquid aromatic deodorizing agent is packed.

In the present invention, the above-mentioned isoparaffin type hydrocarbon is mixed with a perfume such as mentioned above at a weight ratio of from 95/5 to 50/50, preferably from 90/10 to 60/40, whereby a liquid aromatic deodorizing agent having a good aromatic deodorizing property and a long effect durability is obtained. This liquid aromatic deodorizing composition is packed in a vessel as shown in FIG. 1 to obtain a final product. Of course, the vessel applicable to the composition of the present invention is not limited to one shown in FIG. 1.

The present invention will now be described in detail with reference to the following Example that by no means limits the scope of the invention.

EXAMPLE 1

Liquid aromatic deodorizing agents were prepared according to recipes shown in Table 2 by using IP Solvents 1016, 1620 and 2028 (supplied by Idemitsu Petrochemical Co.) having boiling point characteristics shown in Table 1 as the isoparaffin type hydrocarbon. Lemon oil was used as the perfume.

TABLE 1

| Boiling Points (°C.) of Isoparaffin Type Hydrocarbons | | | |
|---|---|---|---|
| | IP 1016 | IP 1620 | IP 2028 |
| Initial Boiling Point | 95 | 166 | 205 |
| 10% Fractionating Point | 108 | 172 | 220 |
| 50% Fractionating Point | 114 | 178 | 230 |
| 90% Fractionating Point | 126 | 185 | 250 |
| Final Boiling Point | 160 | 208 | 260 |

TABLE 2

| Recipes of Deodorizing Agents (parts by weight) | | | | | | | | | | |
|---|---|---|---|---|---|---|---|---|---|---|
| | Sample No. | | | | | | | | | |
| Components | 1 | 2 | 3 | 4 | 5 | 6 | 7 | 8 | 9 | 10 |
| IP 1016 | 80 | 70 | 60 | | | | | | | |
| IP 1620 | | | | 80 | 70 | 60 | | | | |
| IP 2028 | | | | | | | 80 | 70 | 60 | |
| Perfume (lemon oil) | 20 | 30 | 40 | 20 | 30 | 40 | 20 | 30 | 40 | 20 |
| Ethanol | | | | | | | | | | 40 |
| Water | | | | | | | | | | 30 |
| Nonionic Surface Active Agent | | | | | | | | | | 10 |

When these samples were allowed to stand still at −20° C. for 24 hours, phase separation or freezing was not caused in any of samples 1 through 9, but the sample 10 became opaque.

These samples 1 through 10 were packed in vessels as shown in FIG. 1 and were allowed to stand still in a chamber maintained at a temperature of 20° C. and a relative humidity of 65% to conduct the aromatic deodorizing test.

The vessel shown in FIG. 1 comprises a vessel body 1 having a length of 104 mm, a width of 35 mm and a height (exclusive of the neck portion) of 25 mm, a sucking core 3 inserted into a neck 2 of the vessel body, an evaporation plate-supporting member 4 fitted in the neck 2 and an evaporation plate 5 supported on said supporting member. As the evaporation plate 5, a nonwoven fabric is used in the state where it is contacted with the sucking core 3.

Figure 2:
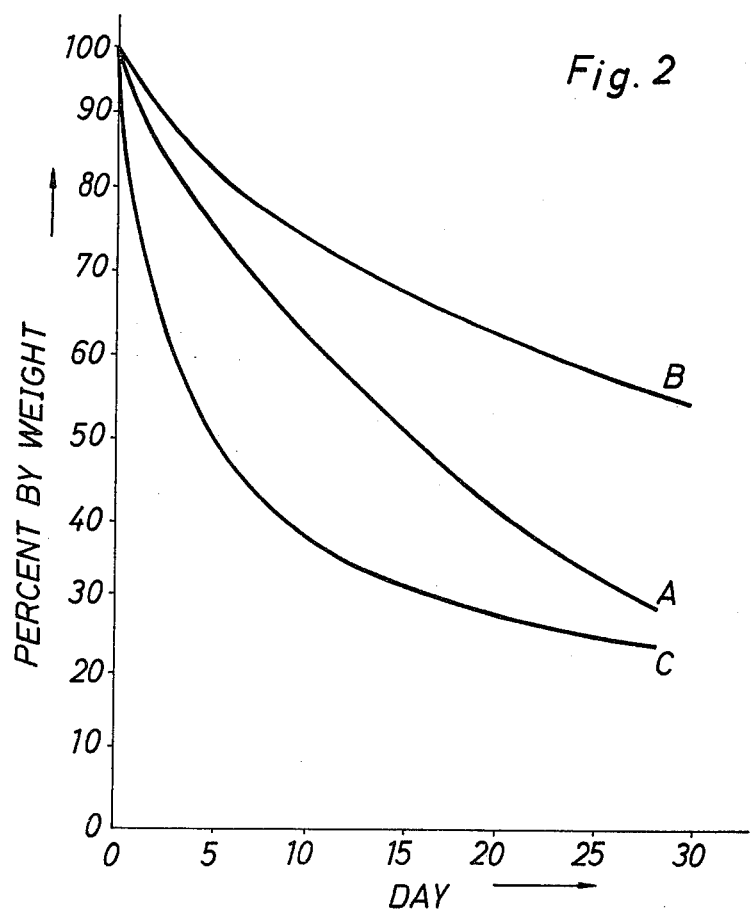
FIG. 2 is a curve showing changes of the weights in liquid aromatic deodorizing agents.

In FIG. 2, curves A, B and C illustrating changes of the weights with the lapse of time in the samples 5, 8 and 10 are shown. From the curve C showing the weight change in the conventional aromatic deodorizing agent solution, that is, the sample 10, it is seen that the rate of consumption of the solution is high in the initial stage in the sample 10 and after passage of a certain period, the nonvolatile surface active agent is accumulated on the evaporation plate or sucking core and the volatility of the solution is drastically reduced. At the organoleptic test, it was confirmed that the aromatic deodorizing effect of the sample 10 was drastically degraded within a short period (about 10 days).

In case of the samples 1 through 3, the solution was consumed within about 15 days, and it was found that the aromatic deodorizing effect was lost within a short period.

As is seen from the curves A and B of FIG. 2, in each of the samples 4 through 9, the solution is gradually evaporated at a substantially constant rate and the composition is excellent in the uniform perfume-releasing property and gradual perfume-releasing property. As the organoleptic test, it was confirmed that these samples were excellent in the durability of the aromatic deodorizing activity. When the solution was analyzed after the organoleptic test of each of these samples, it was found that the composition was not substantially different from the original composition of the solution packed in the vessel.

What is claimed is:

1. A liquid aromatic deodorizing composition having a uniform releasing property, which comprises a solution containing an isoparaffin type hydrocarbon having an initial boiling point higher than 150° C. and a final boiling point lower than 300° C. and a perfume at a weight ratio of from 95/5 to 50/50.

2. A liquid aromatic deodorizing composition as set forth in claim 1, wherein the isoparaffin type hydrocarbon has an initial point higher than 160° C. and a final boiling point lower than 270° C.

* * * * *